(12) United States Patent
Briaud et al.

(10) Patent No.: US 7,299,686 B2
(45) Date of Patent: Nov. 27, 2007

(54) SYSTEM AND METHOD FOR TESTING THE COMPACTION OF SOIL

(75) Inventors: Jean-Louis Briaud, College Station, TX (US); Patrick Briaud, College Station, TX (US); Yanfeng Li, Austin, TX (US); Andrew Fawcett, College Station, TX (US); Matthew L. Potter, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 11/069,075

(22) Filed: Mar. 1, 2005

(65) Prior Publication Data

US 2005/0199045 A1  Sep. 15, 2005

Related U.S. Application Data

(60) Provisional application No. 60/549,319, filed on Mar. 2, 2004.

(51) Int. Cl.
*G01N 3/00* (2006.01)
*G01N 33/24* (2006.01)

(52) U.S. Cl. .......................................... 73/84; 73/12.13
(58) Field of Classification Search .................... 73/84, 73/862.624, 12.13, 12.09
See application file for complete search history.

(56) References Cited

U.S. PATENT DOCUMENTS

| | | | | |
|---|---|---|---|---|
| 2,117,985 A | * | 5/1938 | Ridenour | 73/84 |
| 2,603,967 A | * | 7/1952 | Carlson | 73/843 |
| 3,214,966 A | * | 11/1965 | Menzies | 73/79 |
| 3,557,612 A | * | 1/1971 | D'Arcy | 73/820 |
| 3,595,071 A | * | 7/1971 | Da Rocha et al. | 73/784 |
| 3,998,090 A | * | 12/1976 | Wislocki | 73/12.12 |
| 4,315,429 A | * | 2/1982 | Morozov et al. | 73/84 |
| 4,353,247 A | * | 10/1982 | De Domenico | 73/84 |
| 4,531,400 A | * | 7/1985 | Nevel | 73/12.13 |
| 4,543,820 A | * | 10/1985 | Handy et al. | 73/84 |
| 5,426,972 A | * | 6/1995 | Heirtzler et al. | 73/84 |
| 5,686,652 A | * | 11/1997 | Pfund | 73/12.04 |
| 5,886,253 A | * | 3/1999 | Joustra | 73/84 |
| 6,925,858 B2 | * | 8/2005 | Miles et al. | 73/84 |
| 2004/0073382 A1 | | 4/2004 | Troxler et al. | |

FOREIGN PATENT DOCUMENTS

JP          62255846 A    * 11/1987

* cited by examiner

*Primary Examiner*—Hezron Williams
*Assistant Examiner*—John Fitzgerald
(74) *Attorney, Agent, or Firm*—Baker Botts L.L.P.

(57) ABSTRACT

A device for determining soil compaction includes a control member fitted with one or more sensors that measure the response of the control member during co-action between the control member and a soil surface. In one embodiment, this response can be flexure as characterized by a measurable parameter such as strain. A measurement module in communication with the sensor or sensors determines a soil modulus for the soil based on the strain measurement from the sensor or sensors. In one arrangement, the control member includes one set of sensors that measure radial strain and another set of sensors that measures hoop strain. The device can also include a load sensor for measuring the load applied to the control member. In one embodiment the measurement module includes a processor that determines soil modulus based the strain measurements and the measured load.

18 Claims, 4 Drawing Sheets

SYSTEM AND METHOD FOR TESTING THE COMPACTION OF SOIL

CROSS-REFERENCE TO RELATED APPLICATIONS

This application takes priority from U.S. Provisional Application Ser. No. 60/549,319, Filed Mar. 2, 2004.

BACKGROUND OF THE INVENTION

1. Field of the Invention

The invention relates generally to soil compaction testing equipment and methods for testing the compaction of soils. In particular aspects, the invention relates to devices and methods for determining the soil modulus of soil.

2. Description of the Related Art

Traditionally, techniques for controlling and monitoring the degree of compaction for soils have involved the measurement of dry density for the soil and the determination of an optimum water content for the soil. The term "soil," as used herein, is intended to apply to a wide variety of substances that are intended to be compacted to a specific degree of density in the course of typical civil construction works, including natural soil, base courses, asphalt, embankments and retaining wall backfill. Using conventional methods for monitoring dry density of the soil, a sample of compacted soil is placed inside a cylindrical steel mold. The weight and water content of the sample are determined in a laboratory. A graph is then generated that plots dry density against water content. From these calculations, a maximum dry density and optimum moisture content are derived.

There has been a recent movement to utilize a soil modulus, rather than dry density, as a measure of soil compaction. One reason for this is that soil modulus is currently used as a basis for overlying pavement upon a subbase of soil. One new tool that is used to measure soil modulus is the H-4140 Geogauge™, or Humboldt Stiffness Gauge, from Humboldt Manufacturing Co. of Norridge, Ill. This device places a toroidal-shaped plate upon the soil to be measured and then induces vibration in the plate using a shaker apparatus. Unfortunately, the Geogauge™ device is expensive and complex.

There is a need to provide improved methods and devices for compaction testing and particularly for measurement of soil modulus. The present invention addresses the problems of the prior art.

SUMMARY OF THE INVENTION

The invention provides a simple and effective device and technique for determining soil modulus, and, in turn, soil compaction. An exemplary compaction testing device is described that includes a ground contacting plate that is interconnected by a rigid rod to a measurement module. The measurement module includes a load cell assembly for determining the compressive force placed upon the rigid rod. The ground contacting plate is provided with a number of strain sensors that detect hoop and radial strain in the plate. The sensors provide the detected strain data to the measurement module. Additionally, the measurement module includes a processor to receive the detected strain data from the strain sensors and load measurements from the load cell. The processor is programmed with models or relationship that use the measured data to determine the soil modulus. The measurement module also provides a display device to provide readings to a user for the above measured parameters and calculated soil modulus. A gripping handle is provided on the measurement module for applying downward force to the rigid rod and plate.

In operation, the compaction testing device is used by placing the ground contacting plate in contact with a section of ground to be tested. A zero strain measurement is taken. Then, a predetermined amount of downward force is applied to the plate via the rigid rod. The plate will deform to some degree in response to the downward force. The amount of deformation of the plate will be dependent upon the degree of compaction of the underlying soil. The measurement module will then compute a soil modulus.

Thus, generally speaking, the present invention in some aspects provides a test device for determining soil compaction that includes a control member, such as a plate, for contacting a surface of the soil. One or more sensors positioned in the control member measure the response of the control member when the control member is pressed against the soil surface. This response can be flexure of the plate as characterized by a measurable parameter such as strain. A measurement module in communication with the sensor or sensors determines a soil modulus for the soil based on the strain measurement from the sensor or sensors. In one arrangement, two sets of sensors are fixed on the plate. One set of sensors measure radial strain and the other set measures hoop strain. The load applied to the control member can be measured by a load sensor.

As noted earlier, embodiments suitable for hand-held use can include a tubular member such as a rod to connect the control member to the measurement module. During manual operation, the user may not orient the test device properly relative to the soil surface. To minimize the damage to the test device or errors in the measurements resulting from misalignment attributable to this and other sources, an articulated joint such as a ball joint can be used to couple the tubular member to the control member. Additionally, a pliant pad can be mated or fixed to a face of the control member to equalize or distribute the pressure applied by the plate to the soil surface.

It should be understood that examples of the more important features of the invention have been summarized rather broadly in order that detailed description thereof that follows may be better understood, and in order that the contributions to the art may be appreciated. There are, of course, additional features of the invention that will be described hereinafter and which will form the subject of the claims appended hereto.

BRIEF DESCRIPTION OF THE DRAWINGS

For further understanding of the nature and objects of the present invention, reference should be had to the following drawings in which like parts are given like reference numerals and wherein.

DESCRIPTION OF THE INVENTION

Figure 1:
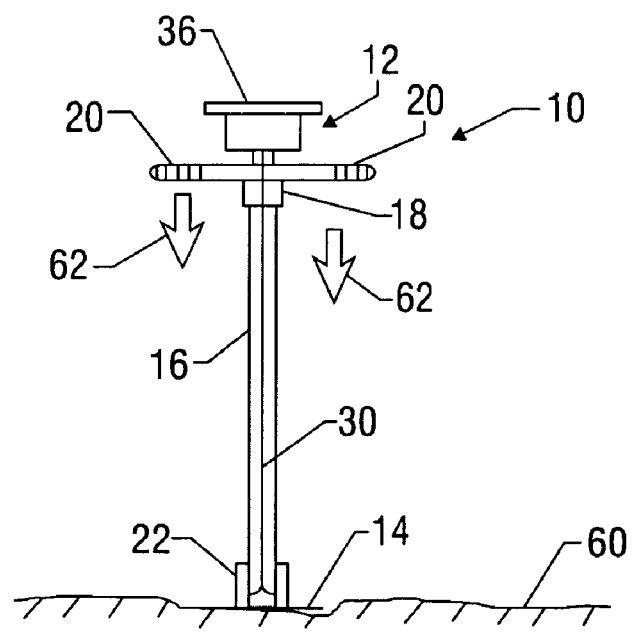
FIG. 1 is an illustration of an exemplary soil compaction testing device constructed in accordance with the present invention.

The present invention relates to devices and methods for determining soil compaction. The present invention is susceptible to embodiments of different forms. Shown in the drawings and described in detail are specific embodiments of the present invention with the understanding that the present disclosure is to be considered an exemplification of the principles of the invention, and is not intended to limit the invention to that illustrated and described herein.

Figure 2:
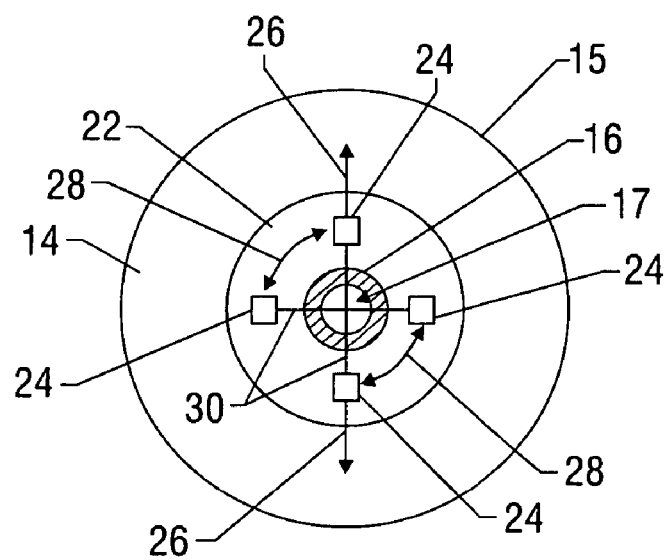
FIG. 2 is a plan view of the ground-contacting plate depicting placement of the sensors associated therewith.

FIGS. 1 and 2 illustrate an exemplary soil compaction testing device 10 constructed in accordance with the present invention. The testing device 10 is lightweight and portable, intended to be easily carried and operated by a single person. The testing device 10 includes a measurement module, shown generally at 12; a ground-contacting plate 14; and a tubular member 16 that interconnects the plate 14 with the measurement module 12. The tubular member 16 can be a relatively rigid rod having a bore for accommodating data carriers such as wiring. In presently preferred embodiments, the rod is a 1 inch-diameter steel rod.

A load cell assembly 18 is incorporated into the testing device 10 below the measurement module 12 to sense the axial load exerted downwardly upon the rod 16. The ground-contacting plate 14 is preferably formed of a substantially rigid, but somewhat flexible metal, such as 2-mm thick steel. The plate 14 has an outer periphery 15 (currently preferred diameter about 152.4 mm) and a center 17, which is welded or otherwise affixed to the lower end of the rod 16. The plate 14 is preferably round in shape. A grippable handle 20 is securely affixed to the rod 16 above the load cell assembly 18 and proximate the measurement module 12.

A protective sensor collar 22 surrounds the rod 16 proximate the ground-contacting plate 14 and houses a plurality of strain-gauge sensors 24 within. The strain-gauge sensors 24 are of a type known in the art that can detect bending strains upon the plate 14 in the radial direction (illustrated by arrows 26) and in the circumferential direction (also referred to as "hoop strain") illustrated by arrows 28. Readings detected by the strain-gauge sensors 24 are transmitted to the measurement module 12 via wiring 30.

It should be understood that the term "plate" is used to describe a control member that co-acts with the soil surface upon application of a suitable force. This co-action can be mechanical in nature such as flexure, compression, expansion, twisting, etc., or some other form of co-action (e.g., electrical). While relatively thin planar members are suitable for such applications and circular shapes can provide manufacturing and handling advantages, no such aspects are necessary attributes for the plate.

Figure 3:
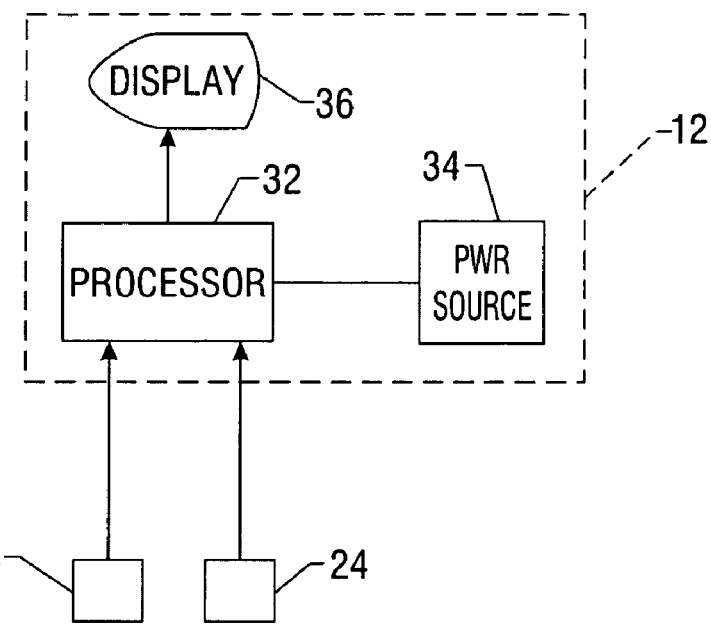
FIG. 3 is a schematic block diagram of the measurement module portion of the soil compaction testing device shown in FIGS. 1 and 2, and associated components.

FIG. 3 schematically depicts the measurement module 12 and associated components. The measurement module 12 includes a processor 32 that receives inputs from the load cell assembly 18 and the strain-gauge sensors 24. A power source 34, such as a battery, is included in the module 12 in order to supply necessary power to the processor 32 and other components. Display panel 36 is also included within the measurement module 12 to provide visual indicators to a user of the device 10 of the parameters sensed by the strain-gauge sensors 24 and the load cell assembly 18. While visual indicators are described below, it should be understood that data can be communicated to the user with non-visual signals, such as auditory or vibratory signals.

Figure 4:
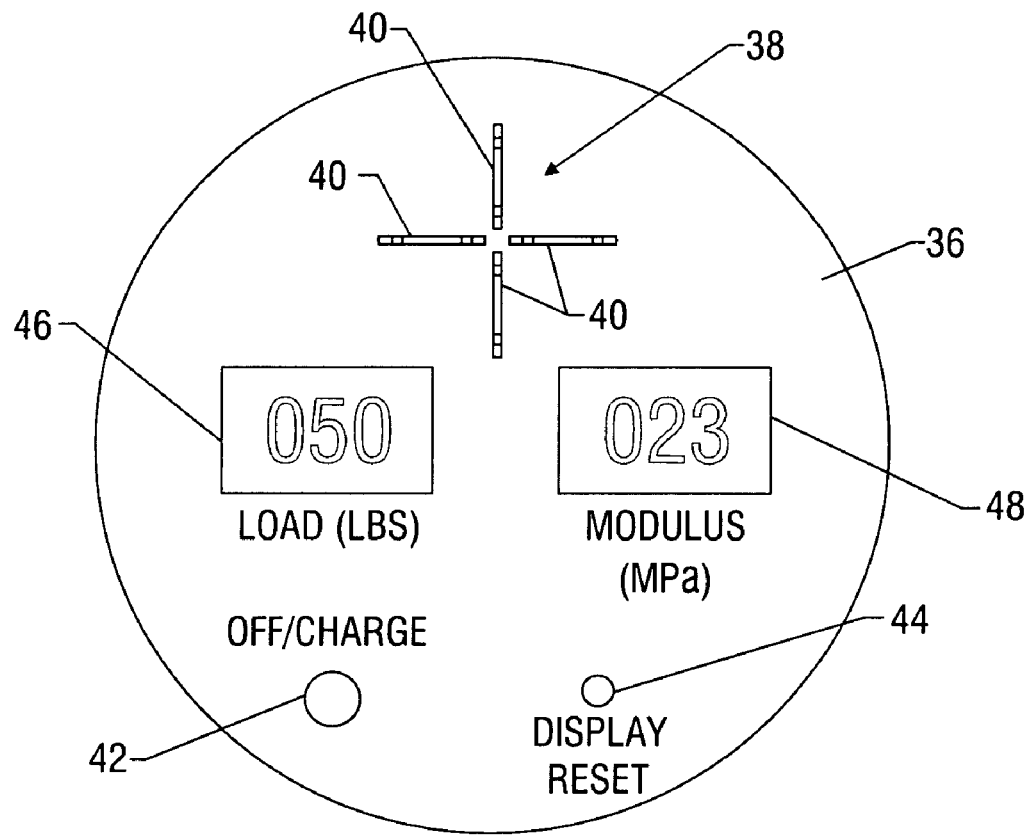
FIG. 4 depicts an exemplary display portion for the measurement module of FIG. 3.

FIG. 4 illustrates an exemplary display panel 36 associated with the measurement module 12. The display panel 36 includes a leveling display portion 38 for proper vertical orientation of the device 10. The leveling display portion 38 may comprise elongated fluid-filled leveling bubbles 40, of a type known in the art. Additionally, an electronic LED-type leveling display might be used for the display portion 38. The leveling display portion 38 is used to ensure that the device 10 is in a substantially vertical position during usage so that the readings obtained by the device 10 are accurate. The display panel 36 includes a power button 42 for turning power to the device 10 off and allowing its power source 34 to be recharged. Also, the display panel 36 includes a display reset button 44 and a pair of display windows 46, 48. The display window 46 provides a visual display of the load detected by the load cell assembly 18. The second window 48 displays the calculated modulus of the soil ($E_{BCD}$). The display panel 36 may, of course, be configured to provide additional or different information to a user. The modulus of the soil ($E_{BCD}$) is related to the measurement of hoop strain by the following equation:

$$E_{BCD} = 277.04 \times p/e - 16.37$$

where: $E_{BCD}$ is the calculated modulus of the soil (in Mpa);
p is the pressure (in kPa) calculated as the load detected by load cell 18 [(kN) divided by the area of the plate ($\pi (0.1524^2/4) = 0.01823$ m$^2$)]; and
e is the hoop strain (in kPa) detected by the sensors 24.

Figure 5:
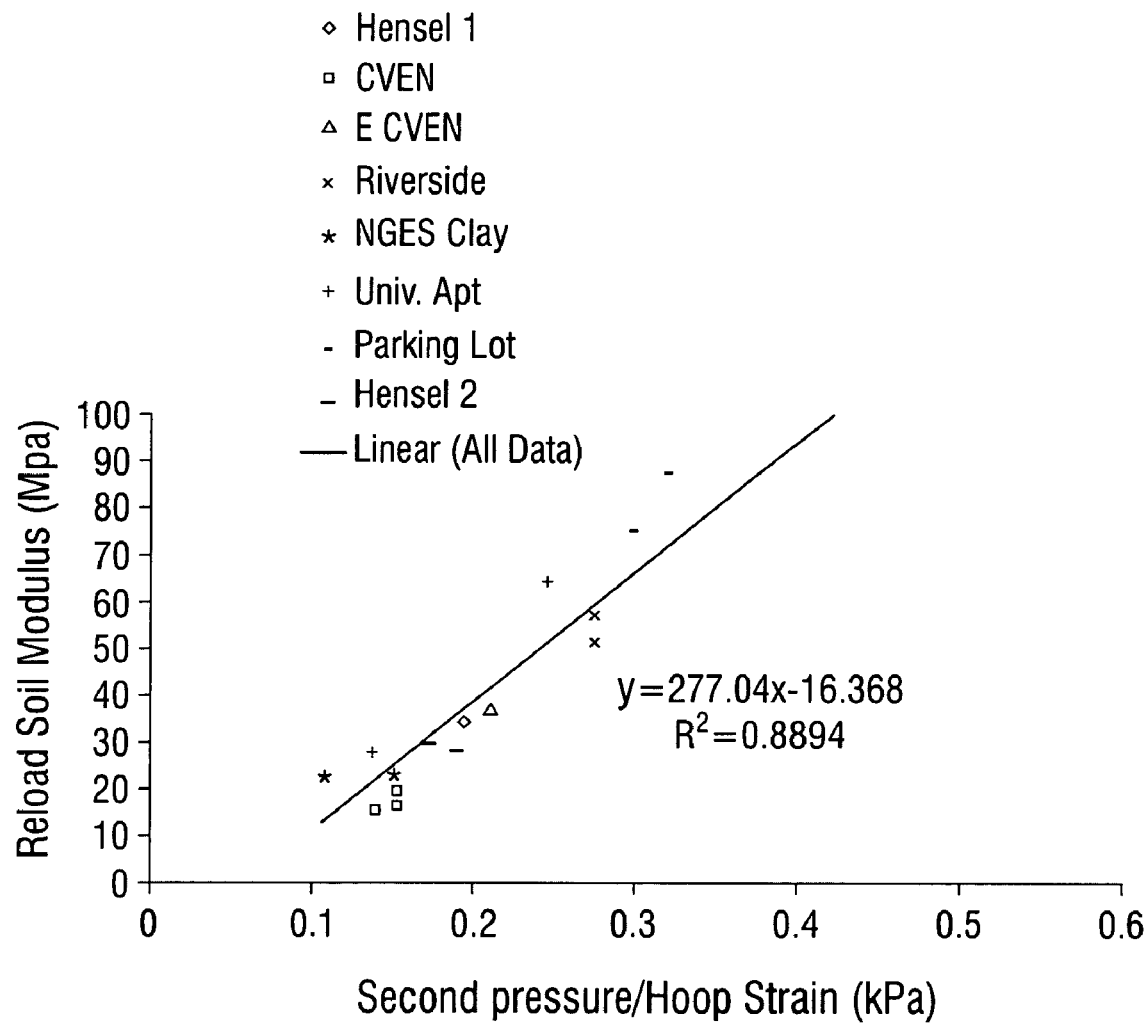
FIG. 5 illustrates the linear relationship between soil modulus, and the ratio of pressure over strain.

Three-dimensional finite element simulations and comparisons to a simple plate test indicate that there is a nearly linear relationship between the bending strains for the plate 14 (i.e., the reload modulus $e_r$) and the modulus of the soil for ground 60 upon which the plate 14 rests during testing. FIG. 5 depicts the linear relationship obtained from the comparison to the plate test.

Thus, it should be appreciated that the present invention encompasses test devices utilizing theoretically and/or empirically derived relationships between soil modulus and parameter of interest such as strain in the plate 14. These formulas or models can be programmed into the processor of the measurement module. The above-described relationships are merely exemplary of the relationships that can be used in accordance with the present invention. Thus, in aspects, the present invention encompasses test devices that use one or more theoretical and/or empirical models or relationships that predict, quantify or otherwise describe the response of a control member to a controlled co-action with the soil. The response can be a measurable change in a parameter of interest such as (e.g., strain, electrical conductivity, shear strength, thermal expansion, etc.). The test device uses these models or relationships in conjunction with the measured response of the control member to the co-action. Depending on the parameter of interest to be measured, the control member can be a plate, a sphere, a cube or other shape.

In operation, the plate 14 of the compaction testing device 10 is first placed in contact with the ground 60, as shown in FIG. 1. A "zero load" reading is obtained, which is the strain readings sensed by the strain-gauge sensors 24 when there is no load exerted upon the handles 20 of the device 10 and, thus, the axial load upon the load cell assembly 18 is essentially zero.

Next, an axial load is applied to the plate 14 via the rod 16. This is typically accomplished by manually pushing the handles 20 downwardly in the direction of arrows 62 in FIG. 1. The display panel 36 will provide a visual reading of the axial load, as measured by the load cell assembly 18 so that a user will be able to determine how much load is being exerted upon the rod 16 and plate 14. A suitable range of values for axial load is from approximately 40 to approximately 60 lbs., and a suitable value for the axial load is approximately 50 lbs. In a further preferred embodiment, the rod 16 and plate 14 are preferably preloaded with the predetermined axial load more than one time. Application of the axial load upon the rod 16 will cause deformation of plate 14 proximate the periphery 15. The deformation will be sensed by the sensors 24 and transmitted to the measurement module 12.

Calibration of device may be, and preferably is, accomplished prior to actual use. To calibrate the device, it is suggested to use a piece of 1 sq. ft. of the calibration rubber pad with an approximate thickness of 3 inches. The plate 14 of the device 10 is pressed downwardly onto the pad, and approximately 50 lbs. of axial load is applied. The resulting hoop strain should be 338 (+/−10), and the modulus reading ($E_r$) should be from 22.5-25 Mpa with a 95% confidence.

Figure 6:
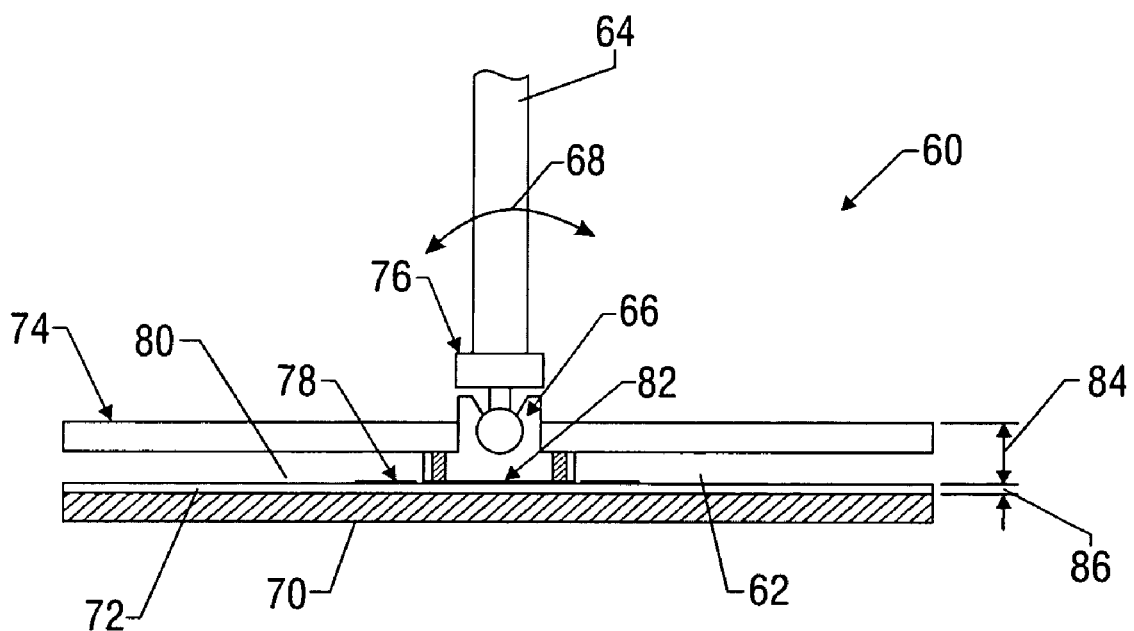
FIG. 6 is an illustration of a section of another exemplary soil compaction testing device constructed in accordance with the present invention.

Referring now to FIG. 6, there is shown a portion of another exemplary embodiment of a soil compaction testing device made in accordance with the present invention. The device 60 includes a control member such as a plate 62 that is coupled to a tubular member 64. The tubular member 64 can be connected to a measurement module described elsewhere. A joint 66 coupling the plate 62 to the tubular member 64 is articulated such that the tubular member 64 can pivot relative to the plate 62. An exemplary direction of pivot is labeled with numeral 68. The articulated joint 66, which can be a ball joint, allows the plate 62 to seat substantially parallel with the soil surface even if the tubular member 64 is not positioned substantially orthogonal to the ground. Thus, advantageously, the joint 66 can reduce bending moments and stress concentrations caused by non-parallel contact between the plate 62 and the soil surface. Such reduction or elimination of bending moments and stress concentrations can increase the accuracy of measurements and minimize the risk of damage to the plate 62. Additionally, a pad 70 can be fixed to the plate 62 to equalize the pressure applied by the plate 62 to the soil surface. The pad 70 can be a pliant member that deforms when compressed between the plate 62 and the ground. The pad 70, which can be made of rubber, can be affixed to the face 72 of the plate 62 with known methods such as adhesives, fasteners, clips, etc. Additionally, a protective plate 74 may be used to shield the plate 72 and related components during handling and storage. In the FIG. 6 embodiment, a load cell 76 is positioned along the tubular member 64 proximate to the joint 66. As previously described, the load cell 76 measures the axial loading being applied to the plate 72. Sensors 78 as previously described are arrayed on an upper face 80 of the plate 62. In certain embodiments, a plaint pad such as a rubber pad 82 can be used between the joint 66 and the plate 62. Also, the distances labeled 84 and 86 can be made adjustable to accommodate a particular design or application.

It should be appreciated that the above described embodiments are merely illustrate some aspects of the present invention. The present invention also, in other embodiments, includes test devices configured to operate without human manipulation. For example, remotely operated vehicles may be fitted with test devices to test soils under human guidance or independently. Furthermore, in some embodiments, the measurement module is not connected to the rod. For instance, the measurement module can be a portable unit carried on the person of the user. Such a measurement module can communicate with the sensors using known telemetry systems such as RF telemetry. Moreover, in some embodiments, a single "central" measurement module can be adapted to communicate with the sensors of a plurality of test devices. In yet other embodiments, non-axial loads, such as torsional and shear loads, can also be used to determine soil modulus.

Those of skill in the art will recognize that numerous modifications and changes may be made to the exemplary designs and embodiments described herein and that the invention is limited only by the claims that follow and any equivalents thereof.

What is claimed is:

1. An apparatus for determining soil compaction of a soil, comprising:
   (a) a control member for contacting a surface of the soil;
   (b) at least one sensor positioned on the control member that measures strain in the control member when the control member is pressed against the soil surface; and
   (c) a measurement module adapted to use a value of a load applied to the control member to determine a soil modulus based on the strain measurements from the at least one sensor.

2. The apparatus according to claim (1) further comprising a display for displaying the determined soil modulus.

3. The apparatus according to claim (1) further comprising a plurality of sensors, the plurality of sensors including at least one sensor for measuring radial strain and at least one sensor for measure hoop strain.

4. The apparatus according to claim (1) wherein the control member comprises a plate configured to flex in a predetermined manner when pressed against the soil surface.

5. The apparatus according to claim (1) further comprising a load sensor coupled to the control member for measuring the load applied to the control member.

6. The apparatus according to claim (1) further comprising a pliant pad fixed to a face of the control member.

7. The apparatus according to claim (1) wherein the measurement module determines the soil modulus based at least in part on the equation EBCD=277.04×p/e−16.37, where EBCD is the modulus of the soil; p is the pressure applied by the control member and e is the hoop strain in the control member.

8. The apparatus according to claim (1) further comprising a tubular member connecting the measurement module to the control member, the tubular member having a bore; and a data carrier extending through the bore for transferring data between the at least one sensor and the measurement module.

9. The apparatus according to claim (8) further comprising an articulated joint coupling the tubular member to the control member.

10. An method for determining soil compaction of a soil, comprising:
    (a) compressing a control member on a surface of the soil;
    (b) measuring strain in the control member when the control member is compressed against the soil surface using at least one sensor positioned on the control member; and
    (c) using a value of a load applied to the control member to determine a soil modulus based on the strain measurement from the at least one sensor.

11. The method according to claim (10) further comprising displaying the determined soil modulus.

12. The method according to claim (10) wherein the measuring strain step includes measuring radial strain and measuring hoop strain.

13. The method according to claim (10) further comprising applying a load to the control member, the load having one of (i) a pre-determined value, and (ii) a predetermined range of values.

14. The method according to claim (10) further comprising measuring the measuring an axial load applied to the control member.

15. The method according to claim (10) further comprising a pliant pad fixed to a face of the control member.

16. The method according to claim (10) wherein the measurement module determines the soil modulus based at least in part on the equation $EBCD = 277.04 \times p/e - 16.37$ where EBCD is the modulus of the soil; p is the pressure applied by the control member and e is the hoop strain in the control member.

17. The method according to claim (10) further comprising a tubular member connecting the measurement module to the control member.

18. The method according to claim (17) further comprising an articulated joint coupling the tubular member to the control member.

* * * * *